(12) United States Patent
Cheng

(10) Patent No.: US 10,485,755 B1
(45) Date of Patent: Nov. 26, 2019

(54) FORMULATION AND METHOD FOR TREATMENT OF NON-ACNE SCARS

(71) Applicant: Wade Cheng, South San Francisco, CA (US)

(72) Inventor: Wade Cheng, South San Francisco, CA (US)

( * ) Notice: Subject to any disclaimer, the term of this patent is extended or adjusted under 35 U.S.C. 154(b) by 0 days.

(21) Appl. No.: 16/242,970

(22) Filed: Jan. 8, 2019

Related U.S. Application Data

(60) Provisional application No. 62/709,855, filed on Feb. 5, 2018.

(51) Int. Cl.
| | |
|---|---|
| *A61K 9/19* | (2006.01) |
| *A61K 9/00* | (2006.01) |
| *A61K 31/19* | (2006.01) |
| *A61K 31/194* | (2006.01) |
| *A61K 31/60* | (2006.01) |
| *A61K 31/045* | (2006.01) |
| *A61M 37/00* | (2006.01) |
| *A61P 17/02* | (2006.01) |

(52) U.S. Cl.
CPC .......... *A61K 9/0021* (2013.01); *A61K 31/045* (2013.01); *A61K 31/19* (2013.01); *A61K 31/194* (2013.01); *A61K 31/60* (2013.01); *A61M 37/0076* (2013.01); *A61P 17/02* (2018.01); *A61M 2037/0023* (2013.01); *A61M 2037/0046* (2013.01); *A61M 2037/0061* (2013.01); *A61M 2210/04* (2013.01)

(58) Field of Classification Search
CPC .... A61K 9/0021; A61K 31/19; A61K 31/194; A61K 31/60; A61K 31/045; A61M 37/045; A61M 2010/04; A61M 2037/0023; A61M 2037/0046; A61M 2037/0061; A61P 17/02
See application file for complete search history.

(56) References Cited

U.S. PATENT DOCUMENTS

| | | | |
|---|---|---|---|
| 4,031,783 A | 6/1977 | Paul | |
| 4,608,370 A * | 8/1986 | Aronsohn | ............ A61K 8/347 |
| | | | 424/DIG. 2 |
| 6,033,421 A | 3/2000 | Theiss | |
| 6,319,942 B1 | 11/2001 | Perricone | |
| 6,521,271 B1 | 2/2003 | Phan | |
| 6,550,356 B1 | 4/2003 | Underwood | |
| 9,144,434 B1 | 9/2015 | Rodan | |
| 10,052,468 B1 | 8/2018 | Rodan | |
| 2004/0092482 A1 | 5/2004 | Gupta | |
| 2008/0161735 A1 | 7/2008 | Lee | |
| 2009/0312691 A1 | 12/2009 | Kim | |
| 2010/0278784 A1 | 11/2010 | Pojasek | |
| 2010/0310680 A1 | 12/2010 | Chen | |
| 2011/0009782 A1 | 1/2011 | Pampalone | |
| 2014/0072613 A1 * | 3/2014 | Lander | ............... A61K 38/1709 |
| | | | 424/446 |

OTHER PUBLICATIONS

Singh et al., Microneedling: Adances and widening horizons, Jul. 8, 2016, Indian Dermatology Online Journal, vol. 7 iss. 4, pp. 244-254. (Year: 2016).*

Tosti et al., Management of Complications of Cosmetic Procedures: Handling Common and More Uncommon Problems, Jul. 13, 2012, Springer Science & Business Media, pp. 1-7. (Year: 2012).*

Council and Gupta, "What's new in the management of acne and acne scarring", in Prime, the International Journal of Aesthetic and Anti-Aging Medicine, Aug. 29, 2017.

\* cited by examiner

*Primary Examiner* — Ali Soroush

(74) *Attorney, Agent, or Firm* — Stephen E. Zweig

(57) ABSTRACT

A chemical formula and method for treatment of non-acne skin scar tissue, in particular, hypertrophic and keloid scars. The chemical formula can comprise a topical chemical solution comprising alcohol, 1,3-dihydroxybenzene, alpha-hydroxy acids, and beta-hydroxy acids. This may be coated on the skin directly, or alternatively the surface of the skin scar can optionally be prepared by puncturing it with a plurality of small holes or micropunctures applied by microneedle or dry needle techniques, and the chemical solution can be applied by a brush or other method. Often a plurality of coatings, with intermediate air drying, may be required to deposit a sufficient amount of chemical during a treatment session. The scar area is then kept dry to help allow the chemical to penetrate, and the scar allowed to heal for about two weeks before any subsequent treatment. Experimental results showing the excellent efficacy of the formula and method are presented.

15 Claims, 5 Drawing Sheets

Figure 1A  Figure 1B  Figure 1C
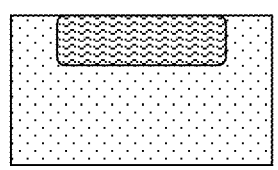
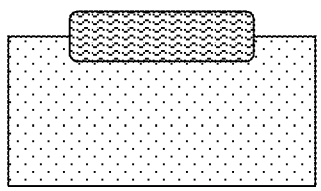
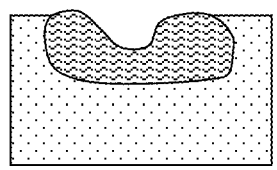
Figure 2
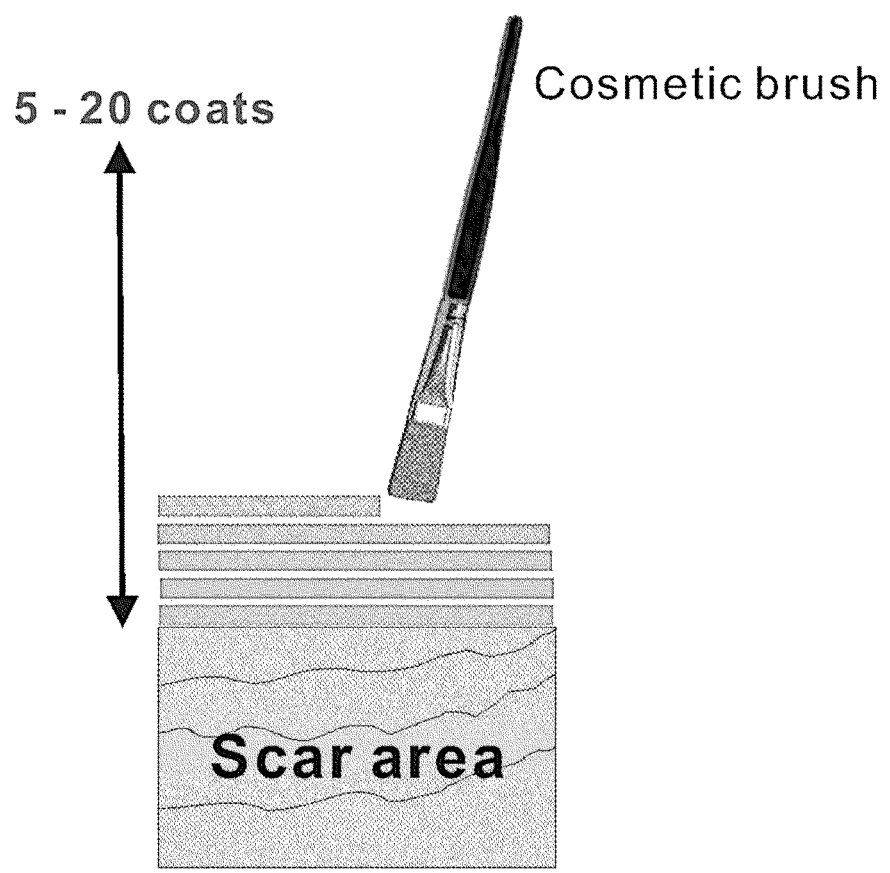

Figure 7A
Figure 7B
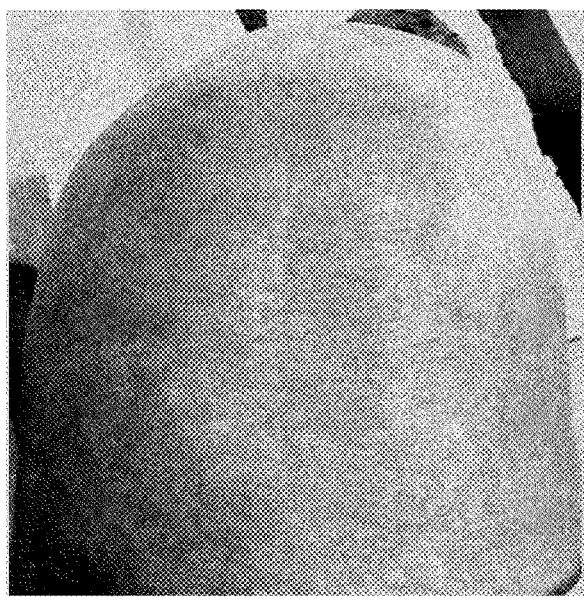

FORMULATION AND METHOD FOR TREATMENT OF NON-ACNE SCARS

CROSS REFERENCE TO RELATED APPLICATIONS

This application claims the priority benefit of U.S. provisional application 62/709,855, filed Feb. 5, 2018, the entire contents of which are incorporated herein by reference.

BACKGROUND OF THE INVENTION

Field of the Invention

This invention is in the field of scar treatment chemical formulations and methods.

Description of the Related Art

Scarring is a very common skin problem. Many types of skin injury can contribute to scarring. These injuries include cuts, burns, acne scars, chickenpox scars, ear piercing, scratches, surgical cuts, tattoo removal, and vaccination sites.

Scars result from the healing process of wound repair in the skin. Scar tissue is composed of the same protein (mostly collagen) as the tissue that it replaces; however, the fiber composition of the protein is different from the uniform and orderly orientation of the collagen fibers found in normal tissue. Scar tissue also lacks elasticity. Sweat glands and hair follicles do not grow back within scar tissues. In addition, collagen may be overproduced or under-produced relative to the surrounding skin level.

Scar tissue often has a color that is different from the surrounding skin. For example, the color of scar tissue is often pink, while the color of the remainder of the skin is often different.

There are several types of scars. Most skin scars are flat (see FIG. 1) and leave a trace of the original injury that caused them. Hypertrophic scars (see FIG. 2) are raised above the surrounding skin. Keloid scars often have a raised appearance that is similar to hypertrophic scars, but Keloid scars can also extend outside of the original wound area, and are thus often regarded as being more severe. Atrophic scars (see FIG. 1C) take the form of a sunken recess in the skin and thus create a "pitted" appearance. Stretch marks (technically called striae) are also a form of scarring.

Scars usually distract from the cosmetic appearance of an individual, and as a result, there is much interest and commercial activity in finding various methods to improve the appearance of scars. Indeed, the website Prescient & Strategic Intelligence (PSI) reports that the US scar treatment market was, as of 2017, a $6.3 billion dollar a year market, and this market was expanding at about a 10.4% annual growth rate. (https://www.psmarketresearch.com/market-analysis/us-scar-treatment-market). According to PSI, companies active in the scar treatment industry include Sonoma Pharmaceutical Inc, Revitol Corporation, Johnson & Johnson, and others.

Generally, hypertrophic scars and keloid scars, which are raised above the skin, are considered particularly unsightly. Unfortunately, according to prior art methods, these types of scars are among the hardest to treat. By contrast, acne scars are easier to treat. This is because most acne scars are atrophic (e.g. "icepick" or "boxcar") type scars. Atrophic scars are sunken or depressed below the skin, prior art methods of scar treatment are often able to handle atrophic scars in a more satisfactory manner.

Current (prior art) treatments for scars include over the counter (OTC) topical skincare formulations, light (e.g. laser) therapy, radiotherapy, and surgery. These are discussed below.

Topical treatment methods: Silicone gel, cream or sheets are among the most common personal care products on the market used to treat scars. Topical products containing vitamin E, Aloe Vera and. onion extract, are also available as well. These products can improve scar appearance, at least to a small degree, after about eight to twelve months of use.

Much of the topical formulation work in the field has been focused on acne and acne scars. Work in the field includes the work of Perricone, U.S. Pat. No. 6,319,942; Chen US patent application 2010/0310680; Phan U.S. Pat. No. 6,521,271; Gupta, US patent application 2004/0092482; Pojasek US patent application 2010/0278784; Rodan, U.S. Pat. No. 9,144,434; Rodan, U.S. Pat. No. 10,052,468; and the like; the contents of these applications are here incorporated herein by reference. Other methods useful for treating acne are reported by Council and Gupta, "*What's new in the management of acne and acne scarring*", in Prime, the International Journal of Aesthetic and Anti-Aging Medicine, Aug. 29, 2017.

Light treatment methods: Laser (ablative or non-ablative) and intense pulsed light (IPL) treatments are often used to treat scars. Both methods utilize light to promote a healing process in scar tissue. These methods can improve scar appearance, but cannot completely remove hypertrophic and keloid scars. Improvement is usually seen after three to seven treatment sessions.

Radiotherapy and steroid injection: These methods are rarely used due to side effects and general ineffectiveness.

Surgical excision: Surgical excision can be an effective scar removal method if it is performed well. However, scar regeneration is a serious drawback of this method, and such regeneration can occur over 50% of the time. Moreover, the cost of surgery can be quite high—often over $5,000 for scar removal, depending on the scar's size.

Other techniques discussed in this application:

Microneedling techniques are known in the art, and various types of microneedle roller devices include Lee, US 2008/0161735; Kim, US 2009/0312691; Pampalone, US 2011/0009782; the entire contents of all of these applications are incorporated herein by reference.

Dry needling techniques are often employed in the micropigmentation and tattoo industry, usually in conjunction with various cosmetic tattoo machines and tattoo machines. Examples of such tattoo machines (here called dry needling devices) include Theiss, U.S. Pat. No. 6,033,421; Paul, U.S. Pat. No. 4,031,783; Underwood U.S. Pat. No. 6,550,356; the entire contents of all of these applications are incorporated herein by reference.

BRIEF SUMMARY OF THE INVENTION

The invention is based, in part, on the insight that although non-surgical prior art methods for treatment of sunken recess type atrophic scars, such as acne atrophic scars, had achieved a fair amount of success, improvements are needed for the treatment of raised hypertrophic, Keloid type scars, and surgical scars.

In some embodiments, the invention may be a method of treatment of non-acne skin scar tissue such as hypertrophic, keloidal, and surgical type scar tissue. This method may comprise, over one or more scar reduction sessions, applying the invention's topical scar reduction chemical solution to the scar tissue. This can be done by, for example, applying an alcohol-based scar reduction chemical solution to the skin scar tissue. This solution is usually applied to at least the surface of the skin scar tissue and can be done by various methods such as by using a brush (e.g. a cosmetic brush).

In these above embodiments, the alcohol-based scar reduction chemical solution can be applied to the scar tissue, and no additional steps to make the scar tissue more permeable may be needed.

However in some optional embodiments, to enhance penetration of the topical chemical solution into the underlying scar tissue, usually before the chemical solution is applied, the scar tissue may first be made more permeable to the chemical solution by creating a plurality of short, small diameter, holes (e.g. about 0.1 millimeter-wide, and about 0.5 to 1.0 millimeter-deep) into the surface of the scar tissue. These small holes allow at least some of the chemical solution to be transported below the surface of the scar tissue, thus ensuring that more of the applied chemical formulation is also received transdermally.

The surface of the scar tissue can be treated by using microneedling roller devices or dry needle devices (e.g. micropigmentation needles, usually driven by a cosmetic tattoo machine) to produce a plurality of short holes (or micropunctures) at low density (e.g. 10 to 100 micropunctures per square centimeter) into the scar tissue. After this initial treatment step, the invention's topical chemical solution can then be applied, often again by way of a brush. This allows at least some transdermal application of the chemical solution to occur. After each brush application (often called a "coat") of the invention's topical chemical solution, often the alcohol in the chemical solution will be allowed to briefly air dry (e.g. evaporate), often with an optional fan or other device. After this, another "coat" may be applied, dried again, and so on. The net result of this process is that over the duration of a treatment session (often between 15 minutes and an hour), the chemicals in the alcohol-based solution become deposited on at least the surface of the scar, where they then stick to the surface of the scar. The chemicals, at least some extent, also penetrate into the scar tissue. The amount of chemical deposited increases as the number of application and drying cycles increase. Often a plurality of such solution application and drying steps will be done over the course of a 15 minute to a 1-hour treatment session.

In some embodiments, the scar-reduction topical chemical solution will comprise a topical chemical solution comprising, 10 to 90% alcohol, and at least any two of: 5 to 25% (by weight) of 1,3-dihydroxybenzene (e.g. 1,3-Benzenediol, resorcinol or resorcin); 5 to 25% (by weight) of alpha-hydroxy acids: and 5 to 25% (by weight) of beta-hydroxy acids.

In a preferred embodiment, however, often all three such chemicals will be dissolved in the alcohol solution. In this preferred embodiment, the invention will comprise an alcohol-based solution or mixture, by weight, of 5 to 25% alpha-hydroxy acids; 5 to 25% beta-hydroxy acids; and 5 to 25% 1,3-dihydroxybenzene.

Other formulation ingredients and other treatment methods will also be described.

BRIEF DESCRIPTION OF THE DRAWINGS

FIG. 1A shows a diagram of a flat scar
FIG. 1B shows a diagram of a hypertrophic or keloid type scar.

FIG. 1C shows a diagram of an atrophic scar.
FIG. 2 shows an example of how the invention's topical chemical formulation may be applied to the surface of a scar using a cosmetic brush.
FIG. 7A and FIG. 7B show a (fourth) example of a human patient's surgical scar before (FIG. 7A) and 21 days after (FIG. 7B) a single treatment-healing session according to the invention.

DETAILED DESCRIPTION OF THE INVENTION

Figure 3A:
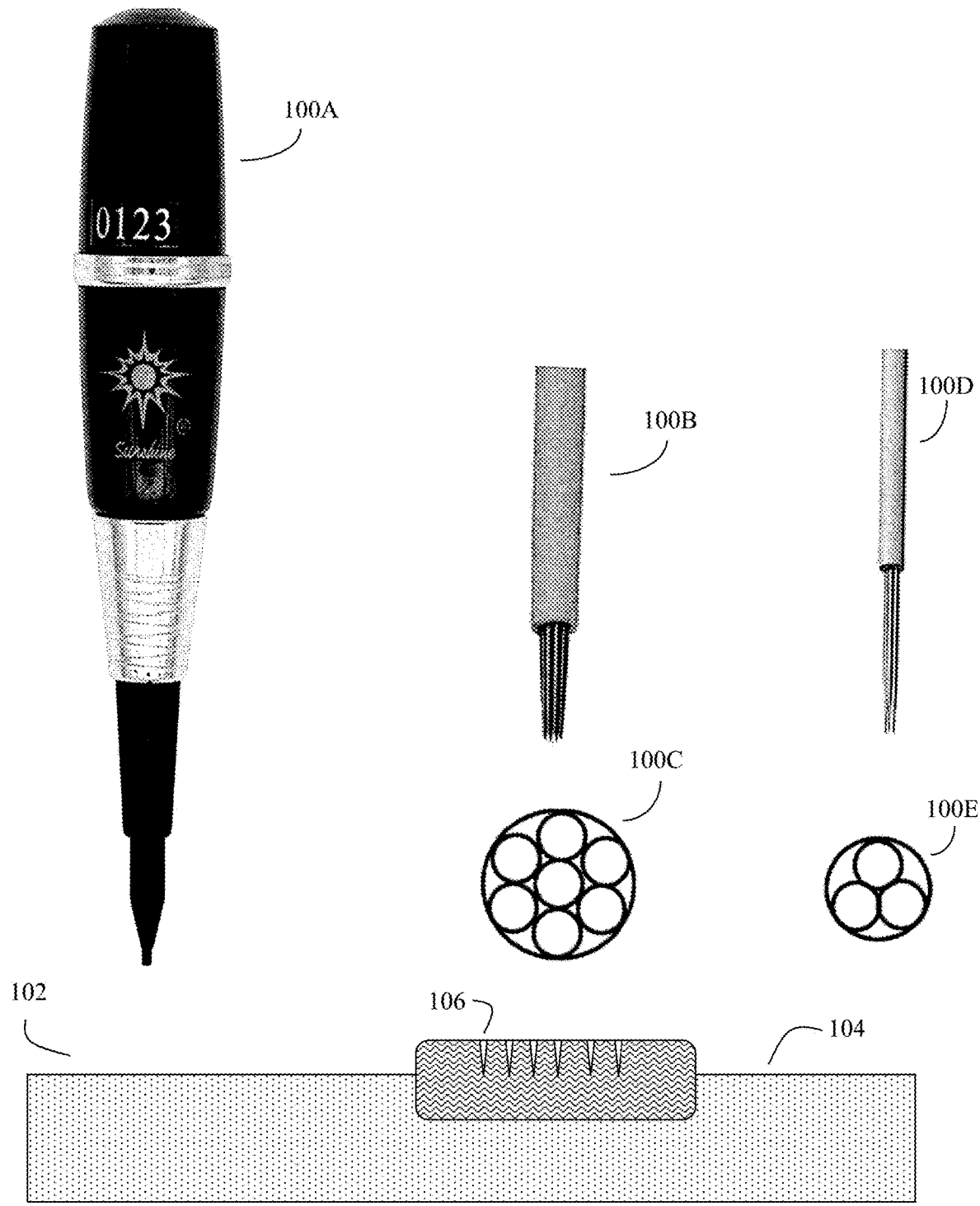
FIG. 3A shows an example of how the invention's topical chemical formulation may be applied on the surface, as well as immediately below the surface, of a hypertrophic or keloid type scar through the use of microneedles applied using a cosmetic tattoo machine. Here a cosmetic tattoo machine, and various types of microneedle attachments (here in a 7 and 3 microneedle, configuration, which creates a series of small (usually 0.5 mm to 1 mm deep) micropunctures on the surface of the scar), are also shown.

An ideal topical or transdermal scar reduction chemical formulation and application method would be able to:
1) Significantly soften or loosen scar tissue (in particular scar collagen protein fibers).
2) Be able to promote the distribution of scar tissue protein fibers in an orderly orientation more closely resembling normal skin proteins.
3) Be able to promote a more uniform height of the scar tissue and associated protein fibers relative to the level of the surrounding skin.

Based upon experimental data, it was found that that the combination of chemicals and skin treatment methods, as disclosed herein, works unexpectedly well for treatment of non-acne type scars. In particular, these methods and chemicals disclosed herein work unexpectedly well, relative to prior art, for normally refractory (hard to treat) scars such as hypertrophic scars, keloidal scars, and surgical scars. Note that the chemicals and skin treatment methods disclosed herein also work well for other types of scars, such as stretch marks, as well.

In some embodiments, the invention may be an alcohol-based topical chemical solution and treatment method for scars. The solution employs one or more alpha-hydroxy acids (such as any of lactic acid, glycolic acid or citric acid), one or more beta hydroxy acids (as salicylic acid or 3-hydroxybutanoic acid), and 1,3-dihydroxybenzene (this is also commonly referred to as called 1,3-Benzenediol, resorcinol or resorcin).

Although topical chemical formulations using a simpler combination of alcohol and only one or two of the other components (e.g. the alpha-hydroxy acids, the beta-hydroxy acids, and the 1,3-dihydroxybenzene components) will have some efficacy, the surprising aspect of the invention is the synergistic effect that occurs when this particular combination of chemicals is used.

In most embodiments, combinations of at least two of these chemicals (the alpha-hydroxy acids, the beta-hydroxy acids, and the 1,3-dihydroxybenzene) will be used, in a preferred embodiment, which produces the most unexpected and strikingly good results, all three of these chemicals (the alpha-hydroxy acids, the beta-hydroxy acids, and the 1,3-dihydroxybenzene) will be used together in the invention's alcohol based chemical formulations.

Each of the various chemicals (e.g. the alpha-hydroxy acids, the beta-hydroxy acids, and the 1,3-dihydroxybenzene), if used, will be present in the above chemical solution in a 5 to 25% concentration by weight. The alcohol-based solvent will typically be one or more low molecular weight alcohols such as ethyl alcohol, propyl alcohol, or 2-propyl alcohol (isopropyl alcohol).

Note that alcohol solutions will normally absorb some water from the atmosphere. This is because alcohols are water miscible, and pure alcohols are somewhat hygroscopic.

Although water is not required as a component of the invention's chemical solution, there is no requirement that anhydrous (dry) alcohol be used. Thus, in some embodiments, the invention may be an alcohol-based scar reduction topical chemical solution for treatment of non-acne skin scar tissue. This solution will typically comprise 10 to 90% alcohol, and at least any two of (and preferably all of): 5 to 25% 1,3-dihydroxybenzene by weight; 5 to 25% alpha-hydroxy acids by weight; and 5 to 25% beta-hydroxy acids by weight. A low concentration of water (e.g. 0 to 5%) is permissible but is not required.

The alcohol component of the topical formulation will typically comprise at least one low molecular weight alcohol selected from the group consisting of ethyl alcohol, propyl alcohol, and 2-propyl alcohol. The alpha-hydroxy acids can typically comprise at least one alpha-hydroxy acid selected from the group consisting of lactic acid, glycolic acid, and citric acid, and the beta-hydroxy acids can comprise at least one beta-hydroxy acid selected from the group consisting of salicylic acid, and 3-Hyrdoxybutanoic acid. As previously discussed, in a preferred embodiment, however, the topical chemical solution will comprise, 5 to 25% alpha-hydroxy acids by weight, and 5 to 25% beta-hydroxy acids by weight, and 5 to 25% 1,3-dihydroxybenzene by weight.

In some specific embodiments, the invention's chemical formulation may be an alcohol-based mixture with an alpha-hydroxy acid comprising lactic acid, a beta-hydroxy acid comprising salicylic acid, and 1,3-dihydroxybenzene (also called resorcinol or resorcin).

In addition to these primary active ingredients, in some embodiments, additional ingredients such as allantoin and licorice extract may also be added. Other inactive ingredients (e.g. coloring, scent, viscosity modifying agents) may also be added as desired. Ingredients to enhance penetration of the active chemicals into the scar tissue may be added.

With sufficient skin penetration into scar tissue, which can be facilitated by an optional transdermal application using microneedling or dry needling methods, this formulation has been experimentally shown to soften or loosen scar tissue (mostly collagen protein fibers), and promote scar tissue reorganization in a more orderly orientation (normalizing protein distribution). This, in turn, promotes a more even distribution of the scar tissue collagen fibers relative to the surrounding skin level and a more pleasing aesthetic appearance.

As previously discussed, in some embodiments, the invention's topical chemical formulation is brushed repeatedly on the surface of a scar area using multiple "coats" or "layers" in order to improve penetration of the chemicals into the scar tissue. Assuming a process (see FIG. 2) in which each coat is applied with a brush, with (often fan assisted) two or more minutes of air drying between applications, the formula application procedure can often take approximately 45 minutes. After the formulation has been applied, the applied scar area should be kept dry (e.g. protected from water contact) for a minimum of 48 hours application to help ensure good penetration of the formulation's chemicals into the scar tissue.

FIG. 2 shows an example of how the invention's chemical formula may be applied to the surface of a scar using a cosmetic brush.

After each treatment session, the scar tissue and surrounding skin are typically allowed a waiting period of about two weeks (this can vary between about 1-4 weeks, and often a period of about 15 days is good) to recover (heal). This healing waiting period typically provides enough time for at least some scar tissue protein reorganization to occur. After this healing waiting period, the formula application process may be repeated, as desired. Although often positive results are seen in as little as one treatment-healing session (e.g. sample application followed by the healing waiting period), often multiple treatment-healing sessions, such as between 1-6 treatment-healing sessions, are often recommended in order to further optimize the results. As previously discussed, these methods have been found to be particularly effective for formerly intractable hypertrophic scars, keloidal scars, and surgical scars.

This technique is a relatively fast and gentle process. As FIGS. 4A to 6B demonstrate, often a significant improvement can be observed after a single treatment-healing session—that is about two weeks to a month (the healing waiting period) after the first initial treatment.

Although the success rate is high, the degree of scar improvement varies depending upon the condition of the original scar condition (e.g. the scar's size, age, and depth). One advantage of the invention's approach is because the invention's methods promote re-orientation and re-distribution of the scar tissue in a relatively natural or non-aggressive way, the chance of scar regeneration or recurrence quite low, relative to other methods such as surgical or laser methods.

The invention's chemical formulations and methods may, of course, be used in conjunction with laser or surgical methods as well, as desired.

Other Types of Topical Skin-Care Treatments During the Waiting Period

In some embodiments, after the initial 48 hours after chemical formulation application has passed, and during the two-week healing waiting period, other types of topical skin-care treatments may optionally also be applied to the treated scar tissue. These other types of topical skin-care treatments may include treatment with Vitamin A complex (see W Cheng and S Depetris, *Vitamin A Complex, Skin Inc. March/April.* 82-88, 1998), as well as other types of topical skin-care treatment including treatment with omega-3 and omega-6 essential fatty acid oil (http://lpi.oregonstate.edu/mic/health-disease/skin-health/essential-/fatty-acids), treatment with topical potassium iodide solutions, and the like.

Optionally Enhancing Scar Reduction Treatment by Micro-Needling or Dry Needling

During the course of development for the present invention, experimental tests showed that the efficacy of the invention's topical chemical solution can be further enhanced if the penetration of the invention's topical chemical solution into the scar tissue is enhanced by various (and optional) microneedling or dry needling techniques.

Micro-needling (mesotherapy) or Dry Needling (by cosmetic tattoo machine) can considerably enhance the penetration or delivery of the invention's topical chemical solution, because such methods can open up a large number of small, 0.5 to 1 mm deep holes, in on the surface of the scar, thus allowing the topical chemical solution to penetrate deeper into the scar tissue. Due to the higher efficiency of topical chemical solution penetration into the tissue, the number of times the chemical solution needs to be applied to the skin during a given session can often be cut in half.

Put alternatively, in some embodiments, the absorption of the previously described topical chemical solution into the scar tissue may be further enhanced by way of a skin treatment mechanism comprising any of a microneedle or a dry needle. This microneedle or dry needle skin treatment mechanism will typically be configured to facilitate the delivery of least some of the topical chemical solution to a depth of at least 0.5 millimeters below a surface of the non-acne skin scar tissue (such as hypertrophic scars and/or keloid scars).

For example, although, during a typical session without microneedling or dry needling, about 15 coating and drying steps may be needed to apply sufficient chemical to the scar surface. However, if microneedling or dry needling techniques are used, only about 5 to 8 "coats" (e.g. about half) of the number of "coats" of topical chemical solution may need to be applied during a given chemical application session. For either process, it is important to allow the treated scar to heal for about two weeks (e.g. around 10 to 30 days) before the next round of treatment, if any.

Dry Needling

In some embodiments, a cosmetic tattoo machine (100A), equipped with a micropigmentation needle (typically 3-7 round), such as a 3-prong needle (100D) may be used. Here this is termed a "dry needle device". Usually, the micropigmentation needle is on a cosmetic tattoo machine, is directed by hand to the scar area, and needle punctures are produced using straight, shallow and quick movements.

FIG. 3A shows an example of how the invention's chemical formula may be applied on the surface, as well as immediately below the surface, of a hypertrophic or keloid type scar (102) through the use of microneedle methods, such as a cosmetic tattoo machine (100A) and various types of associated microneedle heads, such as a seven-microneedle head (100B, 100C) and a three-microneedle head (100D, 100E). The tattoo machine (100) and associated microneedles can be hand guided to create a series of small (usually 0.5 mm to 1 mm deep) punctures (106) on the surface of the scar. Note how the scar (102) is raised above the surface of the skin (104).

One advantage of dry needling is that it is easier to precisely control where the micropigmentation needle hits the scar, thus minimizing any punctures on the non-scared skin surrounding the scar area.

Microneedling

In some embodiments, a microneedling roller device, with microneedles approximately 0.5 to 1 millimeter long, such as the Dermaroller (Dermaroller GmbH, Germany), or another brand, may alternatively be used. The Dermaroller is a hand-operated cylindrical roller configured with approximately 192 microneedles in eight rows. Each needle has dimensions of approximately 0.1 millimeter in diameter and a length (depending on the model used) between 0.5 to 2 millimeters. As previously discussed, lengths between 0.5 and 1.0 millimeters have typically been found to be most suitable, although longer lengths are not disclaimed, and may be used if desired.

Typically, the microneedling roller is applied over the scared area twice, where it opens up a plurality of small holes (often about 30 micropunctures per square centimeter) on the surface of the scar. After this rolling step, the invention's topical chemical solution is then applied, here again usually by brush application (as per FIG. 2) as a plurality of layers or "coats" (such as 5-8 layers), with drying between the application of each "layer" or "coating".

Figure 3B:
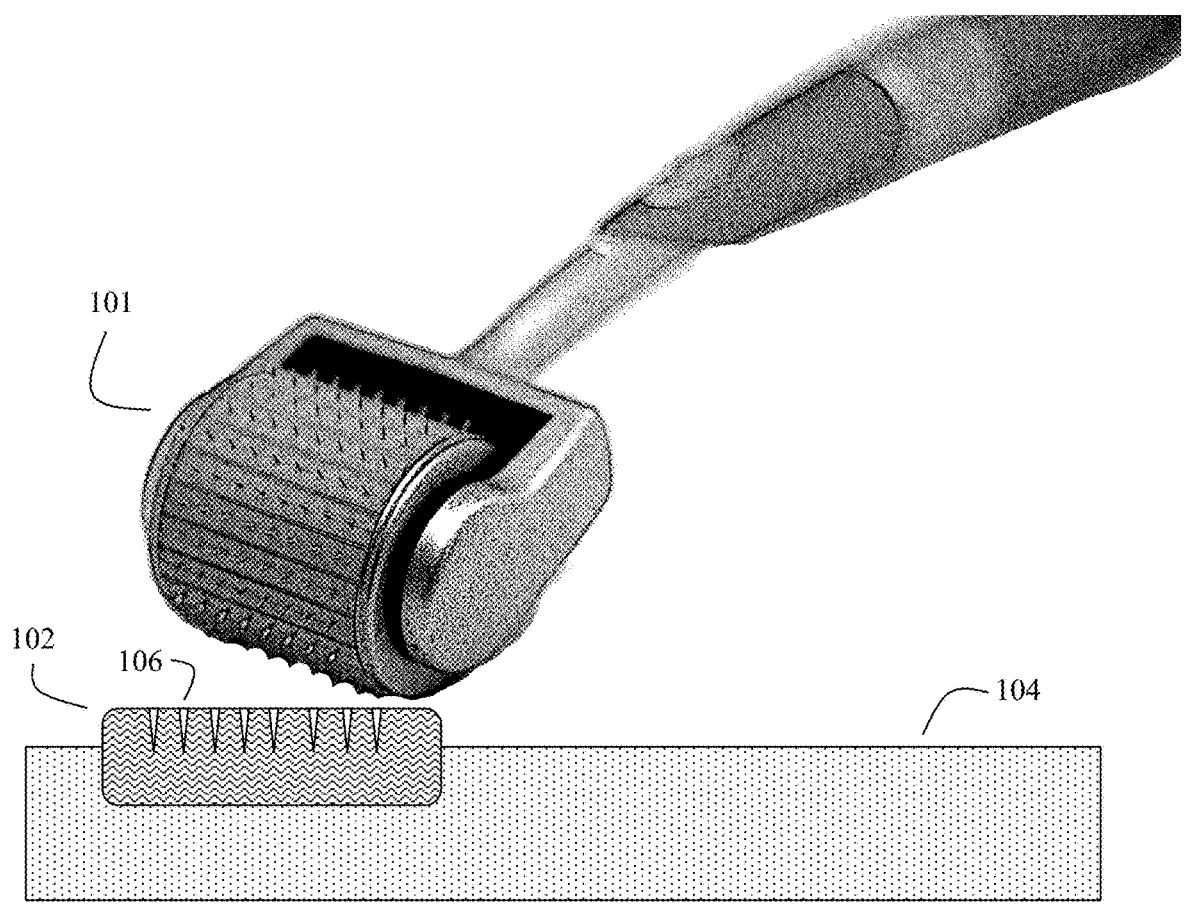
FIG. 3B shows an example of how the invention's topical chemical formulation may be applied on the surface, as well as immediately below the surface, of a hypertrophic or keloid type scar through the use of other types of microneedle methods or dry needle methods. Here a microneedle roller device, which creates a series of small (usually 0.5 mm to 1 mm deep) micropunctures on the surface of the scar, is shown.

FIG. 3B shows an example of how the invention's chemical formula may be applied on the surface, as well as immediately below the surface, of a hypertrophic or keloid type scar (102) through the other methods, such as a microneedle roller (101), which creates a series of small (usually 0.5 mm to 1 mm deep) punctures (106) on the surface of the scar. Note again how the scar (102) is raised above the surface of the skin (104).

Thus, in some embodiments, the invention may be a method of treatment of non-acne skin scar tissue. This method will typically comprise applying a scar reduction topical chemical solution to the scar tissue, over at least one scar reduction session, by (during each scar reduction session) first applying an alcohol-based scar reduction topical chemical solution to the skin scar tissue, and then allowing at least the alcohol in the alcohol-based scar reduction chemical solution to evaporate. This process ends up depositing the chemicals in the scar reduction chemical solution on at least the surface of the non-acne skin scar tissue during this scar reduction session. Often these first two steps will be repeated a plurality of times (such as 5-20 times) during this scar reduction session. This results in a build-up of a plurality of these chemical deposits on at least the surface of the skin scar tissue. As previously discussed, this scar reduction chemical solution will typically comprise 10 to 90% alcohol, and at least any two of 5 to 25% 1,3-dihydroxybenzene (by weight); 5 to 25% alpha-hydroxy acids (by weight), and 5 to 25% beta-hydroxy acids (by weight).

Although the non-acne skin scar tissue can comprise a wide variety of non-acne scars, including stretch mark type scars, the invention produces the most striking results with those non-acne hypertrophic scars raised above a level of the skin surrounding the scar, as well as keloid scars that grow outside of an area of an original wound.

In most embodiments, the alpha-hydroxy acids comprise alpha-hydroxy acids selected from the group consisting of lactic acid, glycolic acid, and citric acid, and the beta-hydroxy acids comprise beta-hydroxy acids selected from the group consisting of salicylic acid and 3-Hyrdoxybutanoic acid. The alcohol will typically comprise low molecular weight alcohols selected from the group consisting of ethyl alcohol, propyl alcohol, and 2-propyl alcohol. In a preferred embodiment, the chemical solution comprises 5 to 25% alpha-hydroxy acids (by weight), and 5 to 25% beta-hydroxy acids (by weight), and 5 to 25% 1,3-dihydroxybenzene (by weight).

As previously discussed, in a preferred embodiment, at least one microneedle (typically a plurality of microneedles, or a dry needle (here both are referred to as a "dry needle device") will be used to produce a plurality of small holes or micropunctures (e.g. 0.1-millimeter diameter, and 0.5 to 1.0 or even 2.0-millimeter diameter deep) from the surface of the scar into the scar tissue. The diameter of the microneedle can vary between 0.05 millimeter to approximately 0.4-millimeter diameter. The number of holes or punctures per square centimeter will often be in the range of 10 to 100 holes (micropunctures) per square centimeter of surface scar tissue, with typical values being around 30 holes or micropunctures per square centimeter of surface scar tissue.

These small holes or micropunctures may be generated immediately before the topical chemical solution is applied to the surface of the scar. The small holes or micropunctures allow the chemical solution to penetrate (e.g. to be transported) deeper into the scar tissue, and thus these methods can be used to apply at least some of the scar-reduction chemical solution below a surface of the scar.

As previously discussed, the at least one microneedle device will typically comprise a plurality of microneedles mounted on the surface of a microneedling roller. The dry needle device can comprise a micropigmentation needle operated with a cosmetic tattoo machine.

After the end of a chemical application session, as previously discussed, the skin will typically be allowed to heal for between 10 to 30 days, and typically at least 15 days, before another scar treatment session will commence. Note that adequate results can often be produced in just one treatment-healing session. If multiple treatment-healing sessions are desired, typically up to about six treatment-healing sessions can be done before diminishing returns set in.

FIGS. 4A to 6B show photographs of actual results obtained with the invention with human patients.

Figure 4A:
FIG. 4A and FIG. 4B show a (first) example of a human patient's scar before (FIG. 4A) and one month after (FIG. 4B) two consecutive treatment-healing sessions according to the invention.
Figure 4B:
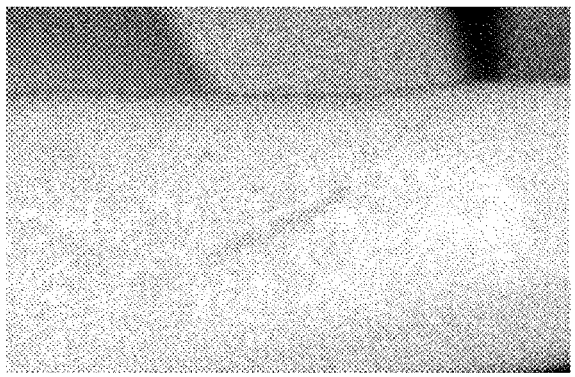

FIG. 4A and FIG. 4B show a first example of a scar before (FIG. 4A) and one month after (FIG. 4B) two consecutive treatment-healing sessions according to the invention.

Figure 5A:
FIG. 5A and FIG. 5B show a (second) example of a human patient's scar before (FIG. 5A) and 15 days after (FIG. 5B) a single treatment-healing session according to the invention.
Figure 5B:
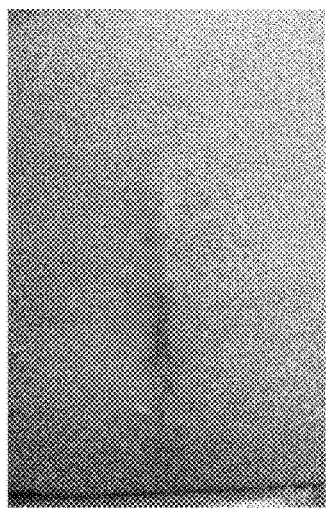

FIG. 5A and FIG. 5B show a second example of a scar before (FIG. 5A) and 15 days after (FIG. 5B) a single treatment-healing session according to the invention.

Figure 6A:
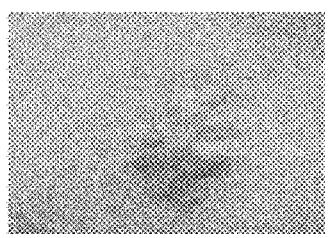
FIG. 6A and FIG. 6B show a (third) example of a human patient's scar before (FIG. 6A) and 30 days after (FIG. 6B) a single treatment-healing session according to the invention.
Figure 6B:
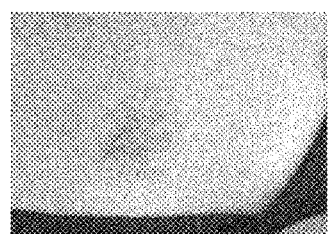

FIG. 6A and FIG. 6B show a third example of a scar before (FIG. 6A) and 30 days after (FIG. 6B) a single treatment-healing session according to the invention.

FIG. 7A and FIG. 7B show a fourth example of a scar before (FIG. 7A) and 21 days after (FIG. 7B) a single treatment-healing session according to the invention. In FIG. 7A and FIG. 7B, the scar tissue was first punctured by dry needling (using a cosmetic tattoo machine) immediately before approximately 5 to 8 coats of the chemical formulation was applied.

The invention claimed is:

1. A method of treatment of non-acne skin scar tissue, said method comprising:
   over a plurality of scar reduction sessions, applying a scar reduction topical chemical solution to said skin scar tissue by the steps of:
   a) applying an alcohol-based scar reduction topical chemical solution to said skin scar tissue;
   b) allowing at least the alcohol in said alcohol-based topical scar reduction chemical solution to evaporate, thus depositing chemicals in said scar reduction topical chemical solution on at least the surface of said skin scar tissue;
   wherein said skin scar tissue comprises any of non-acne hypertrophic scars raised above a level of the skin surrounding said scar, surgical scars, and keloid scars that grow outside of an area of an original wound;
   c) repeating steps a-b so as to produce a plurality of said deposits on at least said surface of said skin scar tissue;
   wherein said scar reduction topical chemical solution comprises:
   10 to 90% alcohol,
   5 to 25% 1,3-dihydroxybenzene,
   5 to 25% alpha-hydroxy acids, and
   5 to 25% beta-hydroxy acids;
   wherein said method promotes the distribution of scar tissue protein fibers in an orderly orientation more closely resembling normal skin proteins.

2. The method of claim 1, wherein said alpha-hydroxy acids comprise alpha-hydroxy acids selected from the group consisting of lactic acid, glycolic acid, and citric acid.

3. The method of claim 1, wherein said beta-hydroxy acids comprise beta-hydroxy acids selected from the group consisting of salicylic acid and 3-Hyrdoxybutanoic acid.

4. The method of claim 1, further using any of a microneedle device, or a dry needle device to prepare said skin scar tissue either before or during application of said scar reduction topical chemical solution, said microneedle device or dry needle device is configured to penetrate at least 0.5 millimeters into said skin scar tissue, thus producing a plurality of micropunctures configured to allow at least some of said scar reduction topical chemical solution to be transported below a surface of said skin scar tissue.

5. The method of claim 1, further using a dry needle device to prepare said skin scar tissue either before or during application of said scar reduction topical chemical solution, said dry needle device configured to penetrate at least 0.5 millimeters into said skin scar tissue, thus producing a plurality of micropunctures configured to allow at least some of said scar reduction topical chemical solution to be transported below a surface of said skin scar tissue;
   wherein said dry needle device comprises a micropigmentation needle operated with a cosmetic tattoo machine.

6. The method of claim 1, further allowing said scar tissue to heal for at least 15 days before repeating steps a-c.

7. A method of treatment of non-acne skin scar tissue, said method comprising:
   over a plurality of scar reduction sessions, applying a scar reduction topical chemical solution to said skin scar tissue by the steps of:
   using a dry needle device to produce a plurality of micropunctures through a surface of said skin scar tissue, said dry needle device configured to penetrate at least 0.5 millimeters past said surface of said skin scar tissue;
   wherein said skin scar tissue comprises any of non-acne hypertrophic scars raised above a level of skin surrounding said skin scar tissue, surgical scars, and keloid scars that grow outside of an area of an original wound;
   a) applying an alcohol-based scar reduction topical chemical solution to said skin scar tissue, wherein said plurality of micropunctures are configured to allow at least some of said scar reduction topical chemical solution to be transported below said surface of said skin scar tissue;
   b) allowing at least the alcohol in said alcohol-based scar reduction topical chemical solution to evaporate, thus depositing chemicals in said scar reduction topical chemical solution on at least a surface of said skin scar tissue;

c) repeating steps a-b so as to produce a plurality of said deposits on at least said surface of said skin scar tissue;

wherein said scar reduction topical chemical solution comprises:

10 to 90% alcohol,
5 to 25% 1,3-dihydroxybenzene,
5 to 25% alpha-hydroxy acids, and
5 to 25% beta-hydroxy acids;

wherein said method promotes the distribution of scar tissue protein fibers in an orderly orientation more closely resembling normal skin proteins.

8. The method of claim 7, wherein said alpha-hydroxy acids comprise at least one alpha-hydroxy acid selected from the group consisting of lactic acid, glycolic acid, and citric acid.

9. The method of claim 7, wherein said beta-hydroxy acids comprise at least one beta-hydroxy acid selected from the group consisting of salicylic acid and 3-Hyrdoxybutanoic acid.

10. The method of claim 7, further allowing said skin scar tissue to heal for at least 15 days before repeating steps a-c.

11. The method of claim 1, wherein said non-acne skin scar tissue comprises surgical scars and keloid scars that grow outside of an area of an original wound.

12. The method of claim 7, wherein said non-acne skin scar tissue comprises surgical scars and keloid scars that grow outside of an area of an original wound.

13. The method of claim 7, wherein said dry needle device comprises a micropigmentation needle operated with a cosmetic tattoo machine.

14. The method of claim 1, wherein said scar reduction topical chemical solution further comprises:

10 to 59% alcohol,
13 to 25% 1,3-dihydroxybenzene,
13 to 25% alpha-hydroxy acids, and
8 to 25% beta-hydroxy acids.

15. The method of claim 7, wherein said scar reduction topical chemical solution further comprises:

10 to 59% alcohol,
13 to 25% 1,3-dihydroxybenzene,
13 to 25% alpha-hydroxy acids, and
8 to 25% beta-hydroxy acids.

* * * * *